US00PP34388P2

(12) United States Plant Patent
Shujun et al.

(10) Patent No.: US PP34,388 P2
(45) Date of Patent: Jun. 28, 2022

(54) ***NELUMBO* PLANT NAMED 'TAOLING SHIPIAN'**

(50) Latin Name: *Nelumbo nucifera*
Varietal Denomination: 'Taoling Shipian'

(71) Applicants: Lu'an Yugarden Horticulture Co., Ltd, Luan (CN); Ninjing Yilianyuan Flower Co., Ltd, Nanjing (CN)

(72) Inventors: Yu Shujun, Luan (CN); Ding Chunxiao, Nanjing (CN); Ding Yuesheng, Nanjing (CN)

( * ) Notice: Subject to any disclaimer, the term of this patent is extended or adjusted under 35 U.S.C. 154(b) by 0 days.

(21) Appl. No.: 17/397,337

(22) Filed: Aug. 9, 2021

(51) Int. Cl.
*A01H 5/02* (2018.01)
*A01H 6/00* (2018.01)

(52) U.S. Cl.
USPC ..... Plt./342

(58) Field of Classification Search
USPC ..... Plt./263.1, 342
See application file for complete search history.

*Primary Examiner* — Karen M Redden

(57) ABSTRACT

A new and distinct cultivar of *Nelumbo* plant named 'TAOLING SHIPIAN' is disclosed, characterized by unique soft coral petals with attractive rose-pink flushing. Flowers have a typical lotus shape, with many petals and petaloids, forming a full flower. The new variety is useful as both an ornamental plant and for cut flower production.

4 Drawing Sheets

Latin name of the genus and species: *Nelumbo nucifera*.
Variety denomination: 'TAOLING SHIPIAN'.

BACKGROUND OF THE INVENTION

The new cultivar, *Nelumbo* 'TAOLING SHIPIAN', is the product of a planned breeding program. The new variety originated from a cross pollination of the unpatented, seed parent, *Nelumbo* 'Dashi' with the pollen parent the unpatented *Nelumbo* 'Muling Oiuse'. The cross pollination was made during July of 2018 in in Nanjing, Jiangsu province, China at a research nursery. The new cultivar 'TAOLING SHIPIAN' was selected in August of 2019 at the same location.

Asexual reproduction of the new cultivar 'TAOLING SHIPIAN' was first performed by root division in in Jiangsu province, China at a research nursery March of 2020. *Nelumbo* 'TAOLING SHIPIAN' has since produced multiple generations and has shown that the unique features of this cultivar are stable and reproduced true to type.

SUMMARY OF THE INVENTION

The cultivar 'TAOLING SHIPIAN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TAOLING SHIPIAN'. These characteristics in combination distinguish 'TAOLING SHIPIAN' as a new and distinct *Nelumbo* cultivar:

1. Typical lotus shaped flower, with many petals and petaloids, forming a full flower.
2. Unique soft coral petals with attractive rose-pink flushing.

PARENTAL COMPARISON

Plants of the new cultivar 'TAOLING SHIPIAN' are similar to plants of the seed parent in most horticultural characteristics. However, plants of the new cultivar 'TAOLING SHIPIAN' differ in the following:

1. *Nelumbo* 'TAOLING SHIPIAN' produces more petals per flower than the seed parent.
2. *Nelumbo* 'TAOLING SHIPIAN' produces petals with a broader diameter than petals of the seed parent.
3. *Nelumbo* 'TAOLING SHIPIAN' produces flowers colored soft coral with rose-pink margins; the seed parent produces greyed-pink flowers with coral margins.

Plants of the new cultivar 'TAOLING SHIPIAN' are similar to the pollen parent in most horticultural characteristics. However, plants of the new cultivar 'TAOLING SHIPIAN' differ in the following:

1. *Nelumbo* 'TAOLING SHIPIAN' produces flowers colored soft coral with rose-pink margins; the pollen parent produces yellow flowers.
2. Flowering stems of *Nelumbo* 'TAOLING SHIPIAN' are shorter than flowering stems of the pollen parent.

COMMERCIAL COMPARISON

The new cultivar 'TAOLING SHIPIAN' can be compared to the unpatented commercial variety *Nelumbo* 'Taopu Jingxiu'. Plants of the new cultivar 'TAOLING SHIPIAN' differ in the following:

1. Flower color of *Nelumbo* 'TAOLING SHIPIAN' is deeper than flower color of 'Taopu Jingxiu'.
2. Flower form of *Nelumbo* 'TAOLING SHIPIAN' is typical lotus-shaped, while flower form of 'Taopu Jingxiu' is a chrysanthemum shape.

BRIEF DESCRIPTION OF THE PHOTOGRAPHS

The accompanying photographs illustrate in full color typical plants of 'TAOLING SHIPIAN' grown outdoors, in the ground in Jingsu Province, China. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Nelumbo* plant. Temperatures ranged from approximately 26° C. to 28° C. night and about 32° C. to 35° C. during the day. No artificial light, photoperiodic treatments or chemical treatments were given to the plants.

DETAILED BOTANICAL DESCRIPTION

Figure 1:
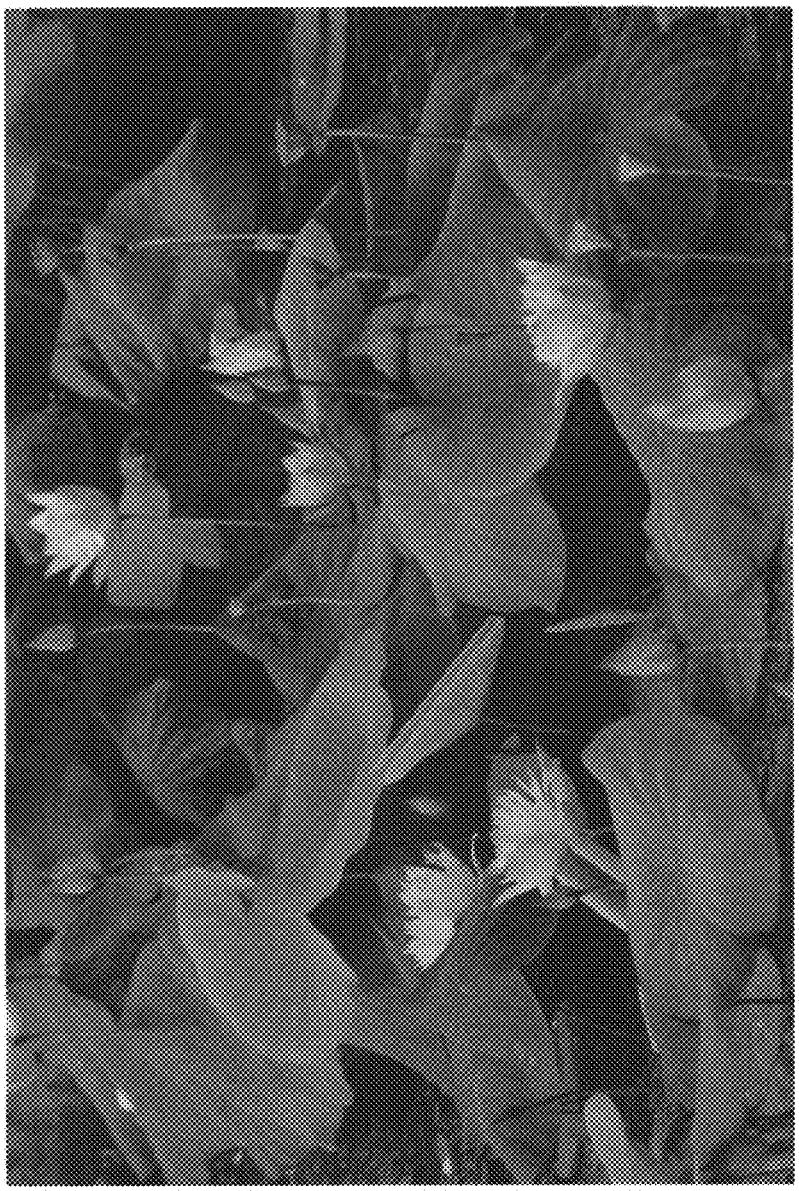
FIG. 1 illustrates in full color a typical of plants of *Nelumbo* 'TAOLING SHIPIAN' beginning to flower at approximately 4 months.
Figure 2:
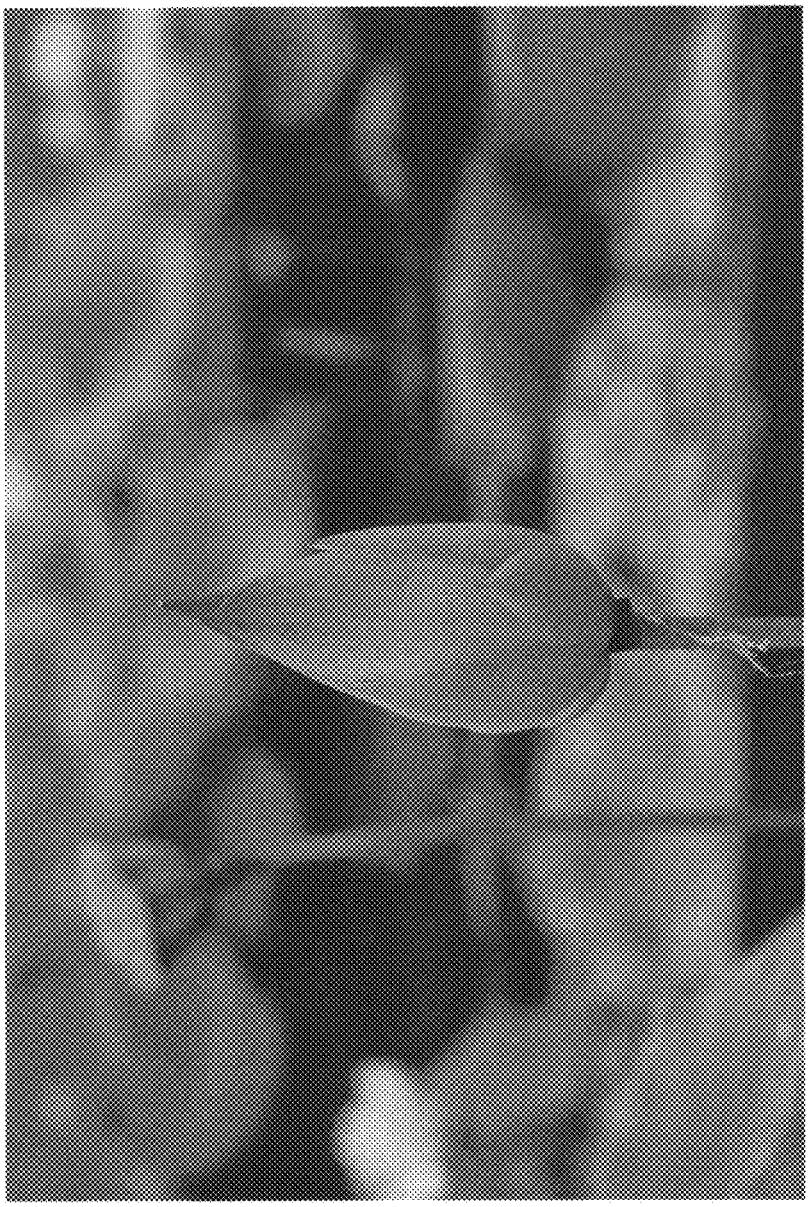
FIG. 2 illustrates in full color a typical flower bud of *Nelumbo* 'TAOLING SHIPIAN'.
Figure 3:
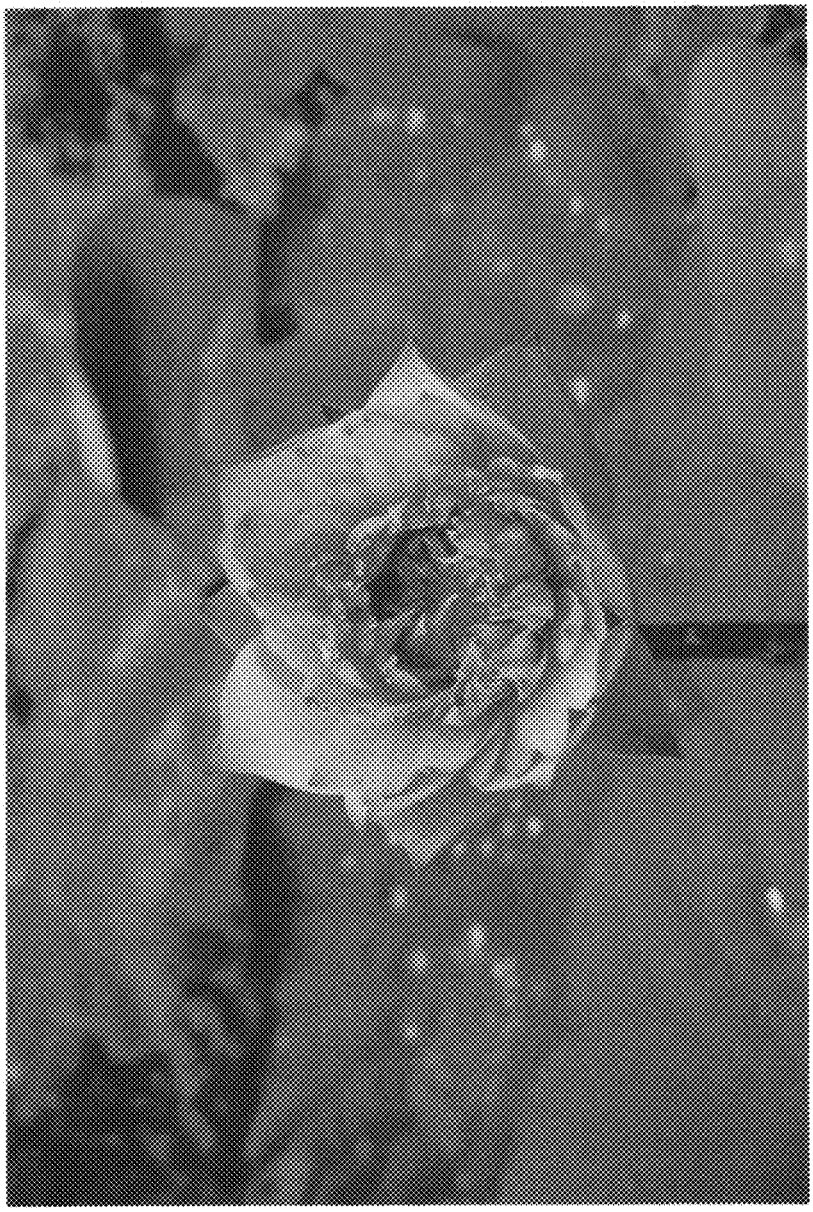
FIG. 3 illustrates in full color a typical opening flower of *Nelumbo* 'TAOLING SHIPIAN'.
Figure 4:
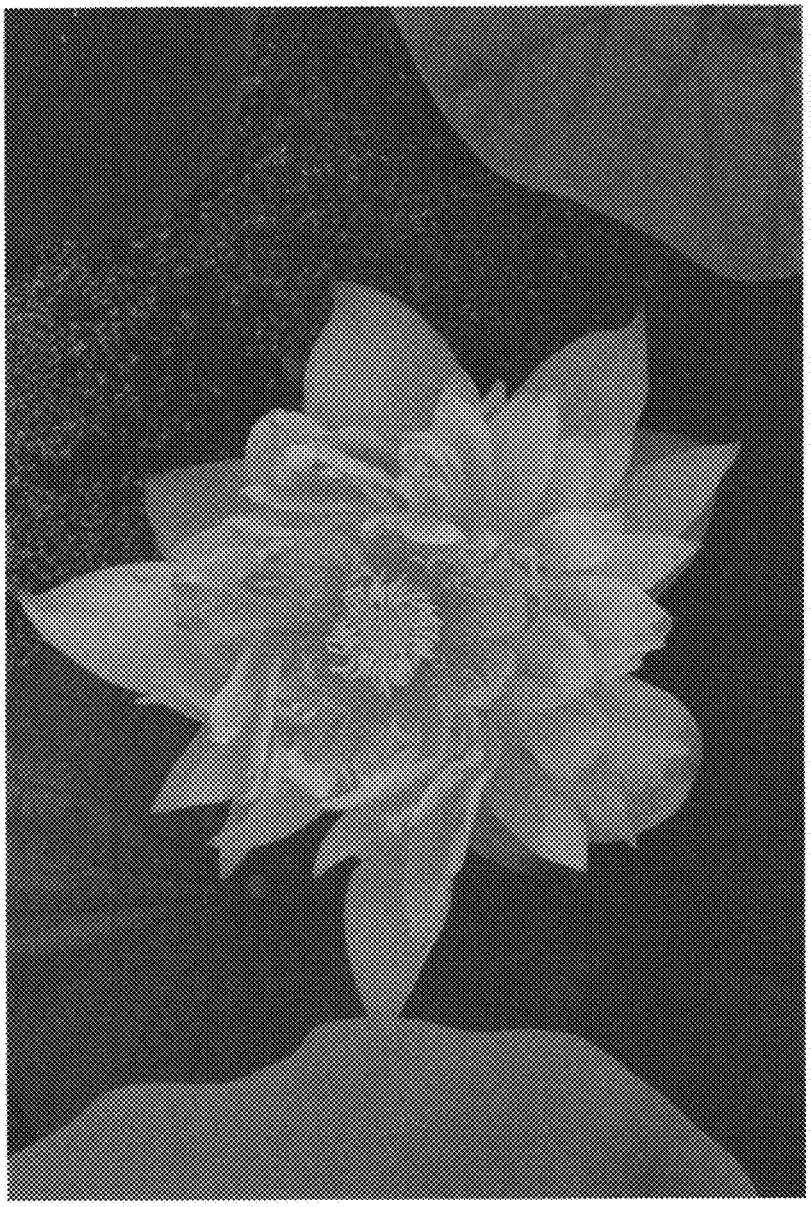
FIG. 4 illustrates in full color typical fully open flower of *Nelumbo* 'TAOLING SHIPIAN'.

In the following description, color references are made to The Royal Horticultural Society Colour Chart, 2001, except where general terms of ordinary dictionary significance are used. The following observations and measurements describe 'TAOLING SHIPIAN' plants grown in an outdoor pond in Jiangsu Province, China. Average day temperature range was around 32° C. to 35° C.; average night temperature ranged around 26° C. to 28° C. No artificial light, photoperiodic treatments or chemical treatments were given to the plants. Natural light conditions were full sunlight. Measurements and numerical values represent averages of typical plant types. Measurements were taken during June to August of 2020.

Botanical classification: *Nelumbo nucifera* 'TAOLING SHIPIAN'.

PROPAGATION

Type of propagation typically used: Root divisions.

PLANT

Age of plant described: Approximately 4 months.

Container size of the plant described: In a pond of approximately 4 meters wide and 90 cm deep.

Growth habit: Flowering pond perennial plant.

Height: Average range 29 to 62 cm.

Plant spread: Approximately 35 to 74 cm.

Growth rate: Moderate.

Root description: Cylindrical rhizomes. New growth near RHS White 155D, mature stems near Grey-Brown N199D.

FOLIAGE

Leaf:

*Arrangement*.—Single, alternate.

*Average length*.—Average 25 to 35 cm.

*Average width*.—22 to 28 cm.

*Shape of blade*.—Obovate.

*Apex*.—Rounded with dimple.

*Base*.—Cuneate.

*Margin*.—Entire, undulate.

*Attachment*.—Sessile sheath.

*Texture of top surface*.—Glabrous.

*Texture of bottom surface*.—Glabrous.

*Color*.—Young foliage upper side: Near RHS Yellow-Green 149B. Young foliage, under side: Near RHS Yellow-Green 149B. Mature foliage upper side: Near RHS Green 136C. Mature foliage, under side: Near RHS Green 136C. Fall foliage upper side: Near RHS Yellow 13A. Fall foliage, under side: Near RHS Yellow 13A.

*Venation*.—Type: Reticulate. Venation color upper side: Near Green 136B. Venation color under side: Near Green 136B.

Petiole:

*Average length*.—Average range 26 cm to 59 cm.

*Average diameter*.—Average range 4 mm to 7 mm.

*Color*.—Upper surface: Near Green 142A. Lower surface: Near Green 142A.

*Texture*.—Glabrous.

FLOWER

Natural flowering season: June through August.

Flower type and habit: Single occurring, double rotate flowers. Upright. Lotus-shaped with center semi-filled with petaloids.

Flowers per plant: 8 to 10 flowers and buds per plant. 14 to 20 stems per square meter produced per year.

Flower longevity on plant: Individual flower about 4 days. Self-cleaning.

*Flower size*.—Height: Approximately 8 cm to 10 cm. Width: Approximately 11 cm to 15 cm.

Bud: (Near opening):

*Shape*.—Ovate.

*Length*.—Approximately 12 cm.

*Diameter*.—Approximately 4 cm.

*Color*.—Near Yellow-Green 149A with tip Red 55B.

Petals:

*Quantity*.—90 to 105.

*Margin*.—Entire.

*Shape*.—Lanceolate to obovate.

*Apex*.—Obtuse.

*Base*.—Tapered.

*Texture*.—Glabrous all surfaces.

*Petal length*.—5.0 cm to 9.8 cm.

*Petal width*.—1.1 cm to 4.5 cm.

*Color*.—Opening: Petal color, upper surface: Yellow-Orange 20D. Red-Purple 60C apical margin. Venation near Red-Purple 60D. Petal color, upper surface: Yellow-Orange 20D. Red-Purple 60C apical flush. Venation near Red-Purple 60D. Fully Open: Petal color, upper surface: Yellow 8D with center near Yellow 4B. Red-Purple 60C apical section. Venation near Red-Purple 60C. Petal color, under surface: Yellow 2D, veins Red-Purple 69D.

Color changes when aging.—Dried flowers Near RHS Greyed-Orange 161C all surface.

Petaloids:

*Arrangement*.—Rotate within interior of flower.

*Quantity*.—10 to 13.

*Length*.—5.0 cm to 7.0 cm.

*Width*.—1.1 cm to 1.4 cm.

*Shape*.—Obovate to lanceolate.

*Margin*.—Entire.

*Apex*.—Acute.

*Base*.—Cuneate.

*Texture*.—Glabrous all surfaces.

*Color*.—When opening: Upper surface: Near Yellow 2D flushed Red 48A. Under surface: Near Yellow 2D flushed Red 53D. Fully opened: Upper surface: Near Yellow 2D. Under surface: Near Yellow 2D flushed Red-Purple 60D.

Sepals:

*Quantity*.—4.
*Length*.—4.6 cm.
*Width*.—2.4 cm.
*Shape*.—Obovate.
*Apex*.—Acute.
*Margin*.—Entire.
*Base*.—Truncate.
*Texture*.—Glabrous all surfaces.
*Color*.—Upper Surface: Near Yellow-Green 144B. Under Surface: Near Yellow-Green 144B.

Peduncle:

*Length*.—Average 60 to 80 cm.
*Width*.—Average 1.0 cm.
*Strength*.—Weak.
*Texture*.—Leathery.

Fragrance: Moderate.

REPRODUCTIVE ORGANS

Stamens: (Androecium).

*Number*.—Average 102 to 112.
*Filament length*.—Approximately 8 to 10 mm.
*Filament color*.—Near RHS Yellow 2D.
*Anther length*.—9 mm to 12 mm.
*Anther width*.—15 mm.
*Anther color*.—Near RHS Yellow 4B.
*Anther shape*.—Elliptic.
*Pollen color*.—Near RHS Yellow 4B.
*Pollen quantity*.—Moderate.

Pistil: (Gynoecium).

*Number*.—Average range 5 to 15.
*Length*.—Approximately 1 cm.
*Stigma*.—Shape: Linear. Color: Near Yellow 13A. Ovary Color: Near RHS Yellow 11D.

OTHER CHARACTERISTICS

Seeds: Not observed.

Temperature tolerance: Tolerates temperatures from approximately −10° C. to at least 40° C.

Disease/pest resistance: Neither resistance nor susceptibility to normal diseases *Nelumbo* observed. Neither resistance nor susceptibility to normal pests of *Nelumbo* observed.

What is claimed is:

1. A new and distinct cultivar of *Nelumbo* plant named 'TAOLING SHIPIAN' as herein illustrated and described.

* * * * *